United States Patent [19]
Skinkle

[11] Patent Number: 6,083,201
[45] Date of Patent: Jul. 4, 2000

[54] MULTI-DOSE INFUSION PUMP

[75] Inventor: David W. Skinkle, Denver, Colo.

[73] Assignee: McKinley Medical, LLP, Wheat Ridge, Colo.

[21] Appl. No.: 09/226,482

[22] Filed: Jan. 7, 1999

[51] Int. Cl.[7] .................................................. A61M 1/00
[52] U.S. Cl. ..................... 604/151; 604/211; 604/118; 604/131; 604/135
[58] Field of Search ..................... 604/110, 121, 604/123, 131, 134, 135, 207, 151, 211, 214, 117, 157, 506; 222/309

[56] References Cited

U.S. PATENT DOCUMENTS

| | | |
|---|---|---|
| 2,428,577 | 10/1947 | Mathis . |
| 2,792,834 | 5/1957 | Kapelsohn . |
| 3,492,876 | 2/1970 | Bull et al. . |
| 4,050,459 | 9/1977 | Sanchez . |
| 4,456,152 | 6/1984 | Young et al. ............................ 222/309 |
| 4,467,942 | 8/1984 | Oshikubo . |
| 4,710,179 | 12/1987 | Haber et al. ............................ 604/211 |
| 4,813,937 | 3/1989 | Vaillancourt . |
| 4,832,694 | 5/1989 | Raphael, III et al. . |
| 4,874,386 | 10/1989 | O'Boyle ................................. 604/246 |
| 4,962,868 | 10/1990 | Borchard . |
| 4,966,585 | 10/1990 | Gangemi . |
| 4,991,742 | 2/1991 | Chang . |
| 4,997,420 | 3/1991 | LeFevre . |
| 5,024,661 | 6/1991 | Wender et al. . |
| 5,104,380 | 4/1992 | Holman et al. ......................... 604/117 |
| 5,135,500 | 8/1992 | Zdeb . |
| 5,178,609 | 1/1993 | Ishikawa . |
| 5,318,544 | 6/1994 | Drypen et al. . |
| 6,001,089 | 12/1999 | Burroughs et al. ..................... 604/506 |

FOREIGN PATENT DOCUMENTS

| | | |
|---|---|---|
| 1 156 298 | 5/1958 | France . |
| 2 561 925 | 10/1985 | France . |

*Primary Examiner*—Wynn Wood Coggins
*Assistant Examiner*—Jennifer Maynard
*Attorney, Agent, or Firm*—Dorr, Carson, Sloan & Birney, P.C.

[57] ABSTRACT

A multi-dose infusion pump employs a piston sliding within the internal chamber of a pump housing to dispense liquid from a port. The peripheral surface of the piston has a sequence of steps in a radial pattern spaced at intervals along the longitudinal axis of the chamber. A cap is rotatably mounted to the pump housing and includes a stop that limits forward movement of the piston by engaging a selected one of the steps on the piston at each rotational position of the cap. This causes a series of predetermined quantities of liquid to be dispensed as the cap is rotated to align the stop with each step in sequence. A spring between the cap and piston urges the piston forward in the chamber to dispense liquid from the port. The peripheral surface of the piston can also be equipped with a series of guide surfaces that allow the piston to be initially retracted toward the cap without engaging the steps while the cap is in an initial rotational position, and then guide the stop along the steps in a predetermined order as the cap is rotated through a progression of rotational positions.

20 Claims, 6 Drawing Sheets

MULTI-DOSE INFUSION PUMP

BACKGROUND OF THE INVENTION

1. Field of the Invention

The present invention relates generally to the field of infusion pumps. More specifically, the present invention discloses an infusion pump capable of administering a series of dosages of liquid medication.

2. Statement of the Problem

Infusion pumps have been widely used for many years to administer antibiotics and other medications to patients. Syringe-type infusion pumps generally include a piston or plunger that slides within a housing to dispense medication. A valve or flow restrictor regulates the flow rate from the pump. Some conventional infusion pumps are driven by a spring, while other infusion pumps require manually pressure to dispense medication.

Another type of conventional infusion pump is vacuum-powered. The pump consists of fluid chamber and a vacuum chamber. Both chambers are equipped with sliding pistons that are mechanically connected (e.g., by a rod) so that a partial vacuum is created in the vacuum chamber as medication is introduced into the fluid chamber. The fluid chamber can be filled either by injecting medication under pressure, or by exerting a force on the fluid chamber piston to simultaneously draw medication into the fluid chamber and create a partial vacuum in the vacuum chamber. After the medication has been loaded into the fluid chamber, the reduced pressure in the vacuum chamber exerts pressure via the pistons and connecting rod that tends to expel medication from the fluid chamber.

Conventional infusion pumps are designed to dispense a single dose of medication, and then must be reloaded for any subsequent doses. This requires additional effort by the healthcare provider. It may entail extra expense if a new infusion pump is used for each dose, or may increase the risk of contamination if the same infusion pump is reused.

Multi-dose infusion pumps have been used in the past in the healthcare industry. However, the multi-dose infusion pumps in common use have substantial shortcomings in terms of complexity, cost, reliability, and ease of use. For example motor-driven infusion pumps can provide flexibility in terms of regulating a series of dosages to be administered to the patient. However, motor-driven infusion pumps tend to be relatively expensive and are complex to use and maintain. Therefore, a need exists in the healthcare industry for an inexpensive, disposable multi-dose infusion pump that is also easy to use.

3. Prior Art

Multi-dose infusion pumps, syringes, and related fluid-dispensing devices that have been used in the past include the following:

| Inventor | Patent No. | Issue Date |
| --- | --- | --- |
| Drypen et al. | 5,318,544 | June 7, 1994 |
| Ishikawa | 5,178,609 | Jan. 12, 1993 |
| Zdeb | 5,135,500 | Aug. 4, 1992 |
| Wender et al. | 5,024,661 | June 18, 1991 |
| LeFevre | 4,997,420 | Mar. 5, 1991 |
| Chang | 4,991,742 | Feb. 12, 1991 |
| Gangemi | 4,966,585 | Oct. 30, 1990 |
| Borchard | 4,962,868 | Oct. 16, 1990 |
| Raphael et al. | 4,832,694 | May 23, 1989 |

-continued

| Inventor | | Patent No. | Issue Date |
| --- | --- | --- | --- |
| Vaillancourt | | 4,813,937 | Mar. 21, 1989 |
| | France | 2,561,925 | Oct. 4, 1985 |
| Oshikubo | | 4,467,942 | Aug. 28, 1984 |
| Sanchez | | 4,050,459 | Sep. 27, 1977 |
| Bull et al. | | 3,492,876 | Feb. 3, 1970 |
| | France | 1,156,298 | May 14, 1958 |
| Kapelsohn | | 2,792,834 | May 21, 1957 |
| Mathis | | 2,428,577 | Oct. 7, 1947 |

Drypen et al. disclose a metering syringe with a plunger having a series of stop surfaces spaced along its length that contact a stop on the syringe tube. The stop surfaces halt forward movement of the plunger at predetermined intervals. The stop surfaces are angularly displaced about the longitudinal axis of the plunger, so that incremental rotation of the plunger permits the plunger to be advanced to the next stop surface.

Ishikawa discloses a medical liquid injector for continuous transfusion that includes a syringe fitted with a piston having a detachable shaft rod, and a cap that can be connected to the proximal end of the syringe. The cap has an elastic pressing device (i.e., a spring) for continuously pressing the piston (after the shaft rod has been remove).

Zdeb discloses an example of a vacuum-powered infusion pump.

Wender et al. disclose a hypodermic syringe having a plunger shaft with a series of horizontal locking grooves. These grooves halt forward movement of the plunger within the syringe barrel at predetermined intervals. At each stop, the plunger must be rotated by 180 degrees to proceed to the next stop.

LeFevre, Gangemi, and Chang disclose examples of spring-powered infusion pumps.

Borchard discloses an apparatus for dispensing a controlled dose of liquid medication that includes a dispenser head which fits over the needle-end of a syringe, and a tube slidably engaged to the dispenser head which encases the piston-end of the syringe. Sliding the tube forward pushes the syringe piston and thereby dispenses liquid from the syringe. The amount of liquid dispensed can be controlled by the pin and slot arrangement between the dispenser head and tube shown in FIGS. 3a and 3b of the Borchard patent.

Raphael et al. disclose a programmed action hypodermic syringe having at least one pin protruding into the bore of the barrel that slidably engages a tracking groove in the plunger.

Vaillancourt discloses an infusion pump powered by an elastomeric bladder.

French Patent No. 2,561,925 discloses a syringe for dispensing a series of doses of medication. As shown in FIGS. 2–5 of this patent, a pin and slot arrangement between the syringe barrel and piston limits the forward motion of the syringe piston and thereby determines the size of each dose. The embodiment shown in FIG. 3 of this patent uses a slot with a series of steps. This embodiment would require that the piston be rotated slightly before dispensing the next dose.

Oshikubo discloses a repeating liquid dispenser having a tubular main body, an actuating member slidably disposed in the main body, and a pressure button on the end of the actuating member projecting out of the upper end of the main body. A spring-loaded rack and pawl mechanism is used to incrementally dispense a quantity of liquid each time that the actuating member is depressed.

Sanchez discloses a hypodermic syringe for administering a plurality of measured doses that includes a barrel and plunger. The size of each dose is controlled by a pin and track mechanism between the barrel and plunger. The track has a plurality of steps controlling forward motion of the plunger within the barrel.

Bull et al. disclose an aliquant discharge device having a syringe with a plunger and a side arm in the upper section of the syringe barrel. In use, the plunger is withdrawn beyond the side arm and suction draws up a blood sample into the syringe. The plunger is then depressed cutting off the vacuum and trapping a known amount of blood in the syringe barrel. This blood specimen is then aliquoted by means of metal stops affixed to the upper end of the plunger that abut on a series of steps as shown in FIGS. 3A–3E of Bull et al.

French Patent No. 1,156,298 discloses another example of a hypodermic syringe with a track mechanism having a series of steps for controlling forward motion of the syringe piston.

Kapelsohn discloses another example of a syringe with a pin and track mechanism to fix the amount of liquid dispensed.

Mathis discloses a liquid-measuring dispenser with a pin and track mechanism for controlling the amount of liquid dispensed.

4. Solution to the Problem

None of the prior art references discussed above show a multi-dose infusion pump having a progression of raised steps on a piston and a rotating cap with a number of stops to selectively engage one set of these steps to dispense a predetermined dose, as shown in the present invention. In particular, none of the prior art shows a multi-dose infusion pump that further includes an arrangement of guides for the cap stops to help ensure that the dosages are administered in proper sequence.

SUMMARY OF THE INVENTION

This invention provides a multi-dose infusion pump that employs a piston sliding within the internal chamber of a pump housing to dispense liquid from a port. The peripheral surface of the piston has a sequence of steps in a radial pattern spaced at intervals along the longitudinal axis of the chamber. A cap is rotatably mounted to the pump housing and includes a stop that limits forward movement of the piston by engaging a selected one of the steps on the piston at each rotational position of the cap. This causes a series of predetermined quantities of liquid to be dispensed as the cap is rotated to align the stop with each step in sequence. A spring between the cap and piston urges the piston forward in the chamber to dispense liquid from the port. The peripheral surface of the piston can also be equipped with a series of guide surfaces that allow the piston to be fully retracted toward the cap without engaging the steps while the cap is in an initial rotational position, and then guide the stop along the steps in a predetermined order as the cap is rotated through a progression of rotational positions.

A primary object of the present invention is to provide a multi-dose infusion pump that is inexpensive to produce.

Another object of the present invention is to provide a multi-dose infusion pump that can be easily used by a healthcare provider with minimal instruction.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Figure 1:
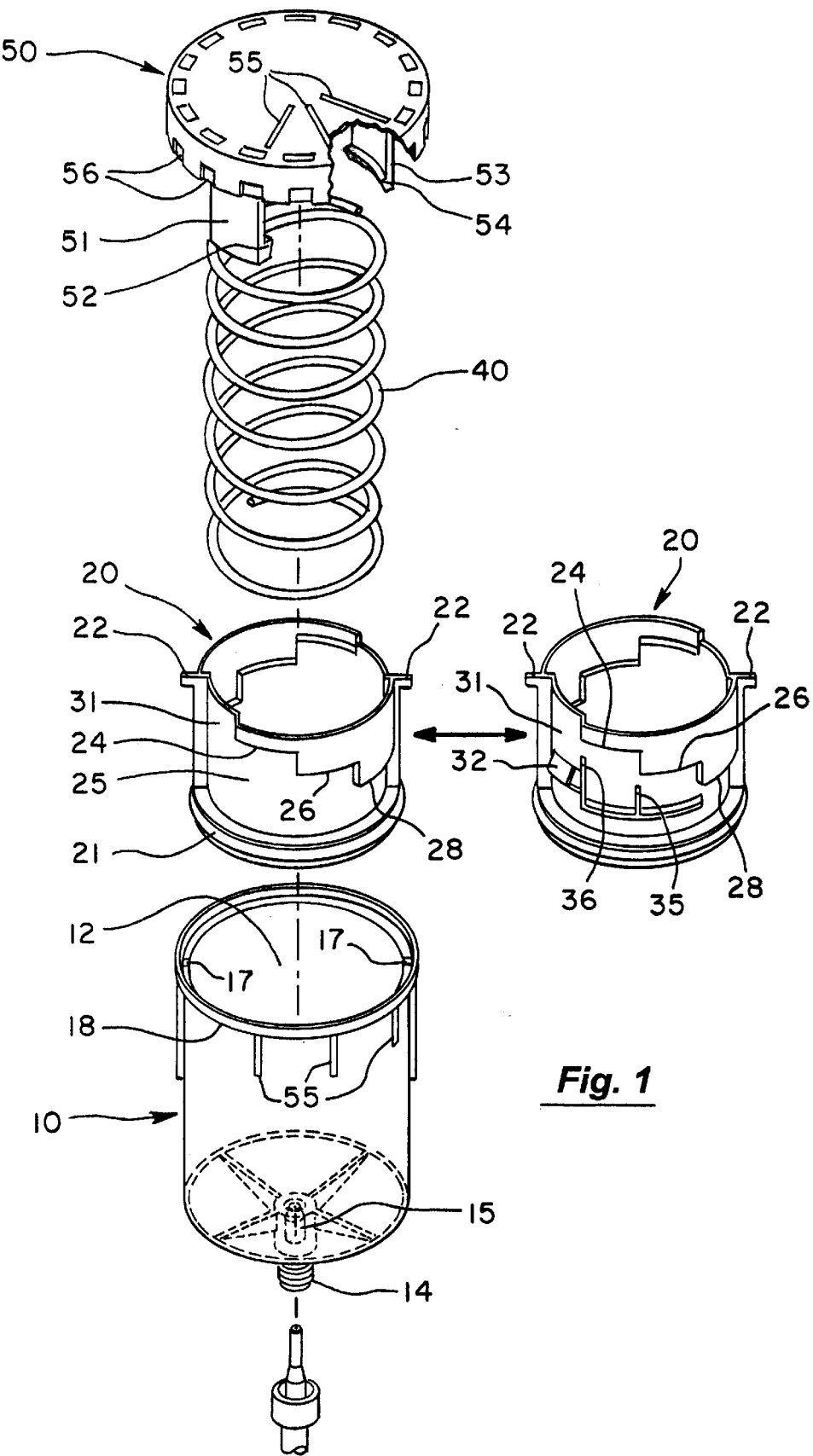
FIG. 1 is an exploded perspective view of the present infusion pump.
Figure 2:
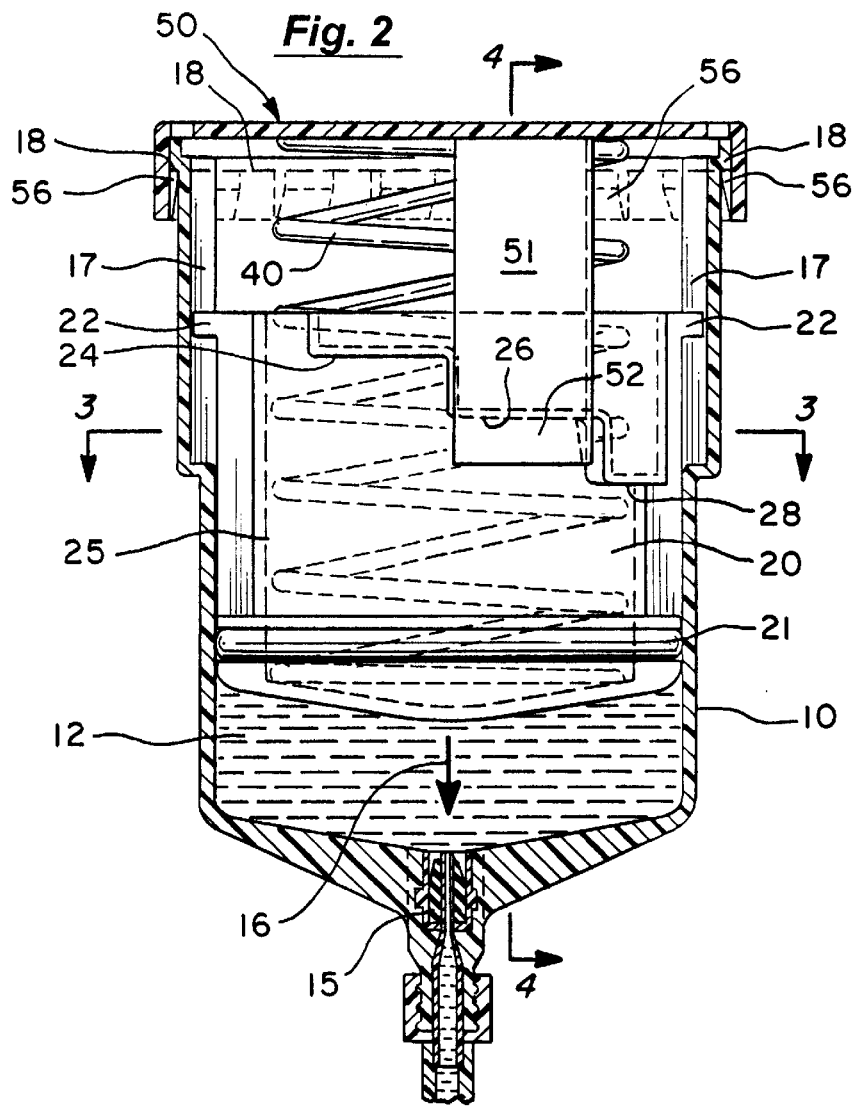
FIG. 2 is a vertical cross-sectional view of the assembled infusion pump.
Figure 3:
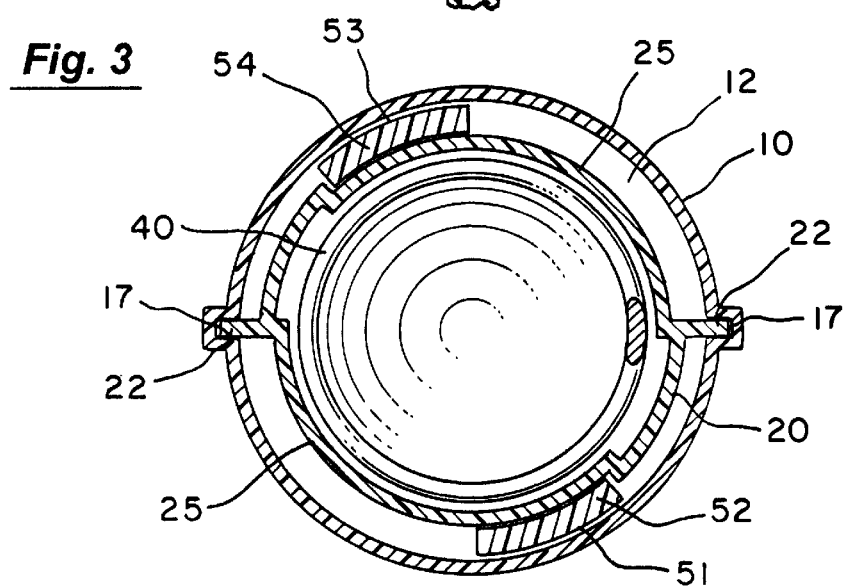
FIG. 3 is a horizontal cross-sectional view of the infusion pump corresponding to FIG. 2 taken along lines 3—3.
Figure 4:
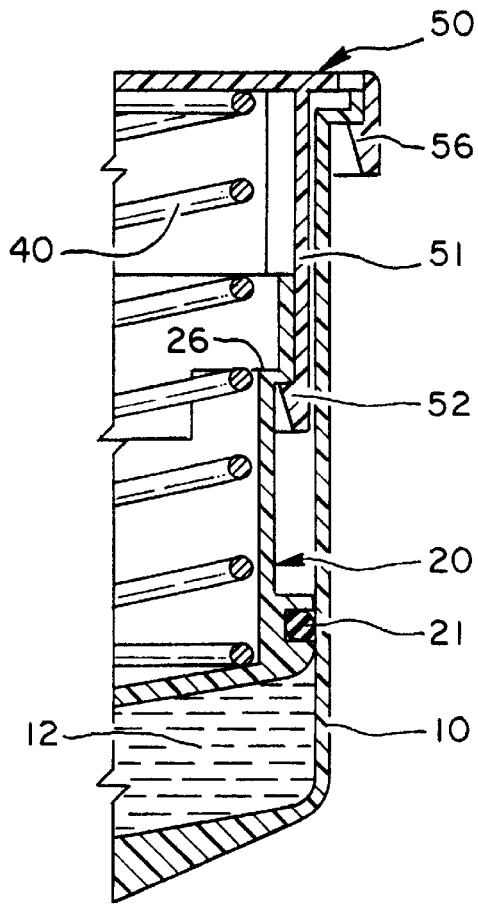
FIG. 4 is a detail vertical cross-sectional view corresponding to FIG. 2 taken along lines 4—4 showing a stop 52 extending from the cap 50 contacting one of the steps 26 on the piston 20.

Turning to FIG. 1, an exploded perspective view is provided of the present invention. FIGS. 2 through 4 are corresponding cross-sectional views of the assembled infusion pump. The infusion pump includes a pump housing 10, which has an internal chamber 12 extending along a longitudinal axis from a proximal opening to a distal port 14 used for dispensing liquid from the chamber 12. A piston 20 slidably engages the internal chamber 12 of the pump housing 10. An O-ring 21 extending about the periphery of the piston maintains a fluid-tight seal against the wall of the pump housing 10. Thus, the piston 20 and pump housing 10 together define an enclosed region suitable for containing a quantity of a liquid medication or fluid. The chamber 12 of the pump housing 10 is typically cylindrical, although other shapes could readily substituted, provided the piston has a complementary cross-section to maintain a fluid-tight seal.

Liquid can be dispensed through the port 14 of the chamber 12 by sliding the piston forward along the longitudinal axis 16, as illustrated in FIG. 2. The port 14 includes a duck-bill valve 15 that prevents liquid from escaping from the chamber 12 while the infusion pump is not in use. An infusion connector can be inserted through the duck-bill valve 15, as shown in FIG. 2, to create an opening that allows liquid to flow from the chamber 12 through the connector and tubing leading to the patient.

Figure 5:
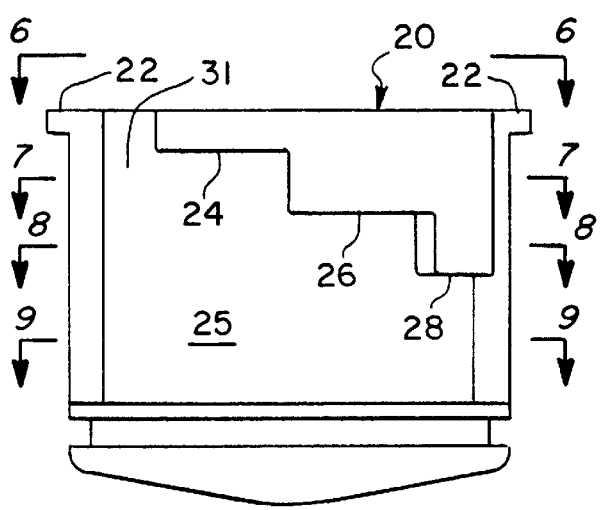
FIG. 5 is a side elevational view of the piston 20.
Figure 9:
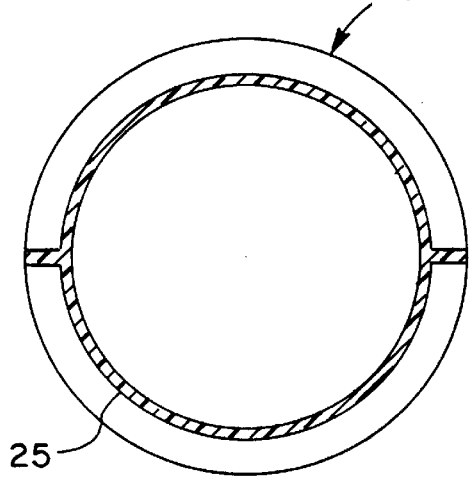
FIG. 9 is a horizontal cross-sectional view of the piston corresponding to FIG. 5 taken along lines 9—9.

FIG. 5 is a side elevational view of the piston 20. FIGS. 6 through 9 are corresponding horizontal cross-sectional views of the piston 20 at various elevations. The piston 20 has a peripheral surface 25 above the O-ring 21 with a progression of raised steps 24, 26, and 28 spaced at intervals in a radial pattern on the peripheral surface 25 of the piston 20. Two tabs 22 extend radially outward from the peripheral surface 25 of the piston to engage corresponding longitudinal slots 17 in the wall of the pump housing 10, as depicted in FIG. 3. These tabs 22 guide the piston 20 so that it can slide along the longitudinal axis 16 within the pump housing 10 and also prevent the piston 20 from rotating with respect to the pump housing 10.

A cap 50 is rotatably mounted over the proximal opening of the pump housing, as shown in FIG. 2. For example, the cap can be equipped with a series of tabs 56 that engage the lip 18 extending around the periphery of the proximal opening of the pump housing 10, shown in FIGS. 2 and 4. The tabs 56 initially clip over the lip 18 of the pump housing when the device is being assembled. However, it is very difficult to subsequently remove the cap 50 from the pump housing 10. The tabs 56 on the cap 50 slide freely relative to the lip 18 on the pump housing 10. This allows the user to easily rotate the cap 50 with respect to the pump housing 10 about the longitudinal axis 16.

A spring 40 compressed between the cap 50 and the rear face of the piston 20 urges the piston 20 forward along the longitudinal axis 16 toward the distal port 14. The volume of liquid dispensed is determined by the degree of forward motion of the piston 20. In particular, the volume dispensed is equal to the cross-sectional area of the piston multiplied by the distance that the piston moves in the axial direction. The flow rate can be controlled by a flow restrictor or valve (not shown) in the tubing downstream from the infusion connector attached to the port 14.

The cap 50 has a number of arms 51, 53 that extend axially forward between the interior surface of the pump housing 10 and the peripheral surface 25 of the piston 20. In the embodiment of the present invention shown in the drawings, the cap 50 has two diametrically-opposed arms, although any number of other configurations could be substituted. A stop 52, 54 extends radially inward from the distal end of each arm 51, 53. Each stop engages a selected one of the raised steps 24, 26, or 28 at each of a plurality of rotational positions of the cap 50. The selected step 24, 26, or 28 then limits forward axial movement of the piston 20 within the chamber 12 to dispense a predetermined quantity of liquid. A series of visual indicia 55 on the cap 50 and outer surface of the pump housing 10 show the proper rotational positions of the cap to align the stops 52, 54 with each of the steps 24–26.

The number of sets of steps 24–26 on the piston 20 typically corresponds to the number of arms 51, 53 and stops 52, 54 extending from the cap 50, so that each stop will engage one set of steps. Thus, the embodiment shown in the drawings has two sets of steps 24–26 located in a diametrically-opposing arrangement on the peripheral surface 25 of the piston 20. In contrast, the number of steps 24–26 in each set is entirely a matter of design choice determined by the number and quantity of dosages that are desired.

The present invention enables a healthcare provider to administer medication to a patient in a series of doses over time from a single infusion pump. By rotating the cap 50, the healthcare provider determines which of the raised steps 24–26 will be engaged by the cap stops 52, 54 as the piston 20 is pushed forward by the spring 40. This limits the range of forward motion of the piston 20 relative to the cap 50, and therefore determines the volume of medication to be dispensed for each rotational position of the cap 50.

The chamber 12 of the infusion pump is initially loaded with medication by the manufacturer or a healthcare provider. The device is assembled with the piston 20 disposed within the pump housing 10 and the spring 40 compressed between the piston 20 and the cap 50. The healthcare provider then connects tubing with an infuser connector to the distal port 14 of the infusion pump, as illustrated in FIG. 2. Pressurized fluid is fed through the tubing into the fluid chamber 12 with sufficient pressure to open the duck-bill valve and overcome the force of the spring 40. Once the pump chamber 12 is filled to a predetermined level, the tubing and infuser connector are removed and the duck-bills of the duck-bill valve 15 return to their sealed position to retain the fluid within the pump chamber 12.

The liquid medication is retained by the duck-bill valve 15 until the infusion pump is ready for use, at which time, tubing with an infuser connector is connected to the distal port 14 of the infusion pump, and the fluid is allowed to flow from the pump chamber 12 as shown in FIG. 2. The device can be filled with a syringe or any other positive-pressure fluid source.

The healthcare provider can select a first dosage by rotating the cap 50 so that each stop 52, 54 is axially aligned with the first raised step 28. This first dosage will then be dispensed through the port 14 as the piston 20 moves forward from its initial, fully-retracted position until the stop 52, 54 comes into contact with the first raised step 28 on the piston 20. At that point, the piston 20 is restrained from further forward movement by the stop 52, 54 and no further liquid is dispensed. The healthcare provider can continue with a second dosage by rotating the cap 50 so that each stop 52, 54 is aligned with the second raised step 26. The second dosage is determined by the incremental distance between the first and second steps 28 and 26 (multiplied by the cross-sectional area of the piston). Similarly, the healthcare provider can continue with a third dosage by rotating the cap 50 so that each stop 52, 54 is aligned with the third step 24. Again, the third dosage is determined by the incremental distance between the second and third steps 26 and 24. Finally, a fourth dosage can be selected by rotating the cap 50 so that the stop 52, 54 is not aligned with any of the steps 24–28. In other words, the stop 52, 54 slides along the longitudinal guide slot 31 without contacting any of the steps 24–26. This allows the piston 20 to move forward until it contacts the distal wall of the chamber 12 and all of the liquid has been dispensed.

For example, the infusion pump can be initially filled with 400 ml of medication. The cap is initially turned to a first rotational position, which will cause the cap stops to engage a first set of raised steps after 100 ml have been dispensed.

The cap can subsequently be rotated to a second rotational position, which will cause the cap stops to engage a second set of raised steps after a second 100 ml have been dispensed. If desired, this process can be repeated two more times to dispense the remaining 200 ml in two 100 ml increments.

The preceding discussion has assumed that the infusion pump will be used to dispense a series of dosages in a predetermined sequence. However, the healthcare provider also has the option of using any single step or any progression of steps. The healthcare provide can rotate the cap to align the stops 52, 54 with any of the steps 24–28. For example, the healthcare provider can dispense a volume of medication equal to both the first and second dosages by rotating the cap to align the stops 52, 54 directly with the second step 26.

Figure 12:
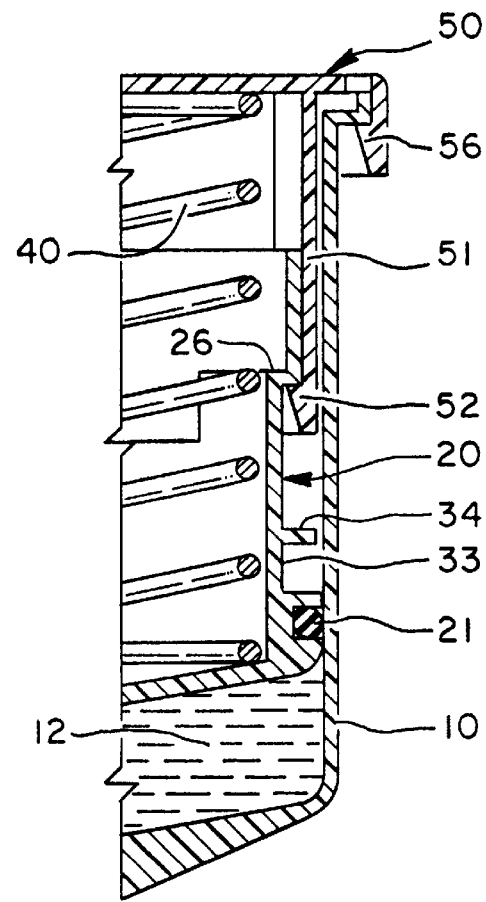
FIG. 12 is detail vertical cross-sectional view corresponding to FIG. 10 taken along lines 12—12, showing a stop 52 extending from the cap 50 contacting one of the steps 26 on the piston 20.
Figure 7:
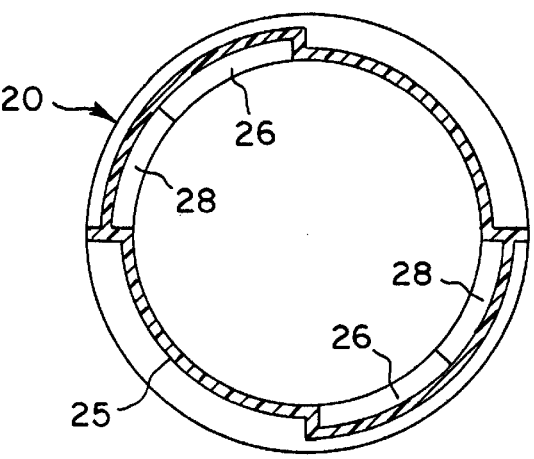
FIG. 7 is a horizontal cross-sectional view of the piston corresponding to FIG. 5 taken along lines 7—7.
Figure 6:
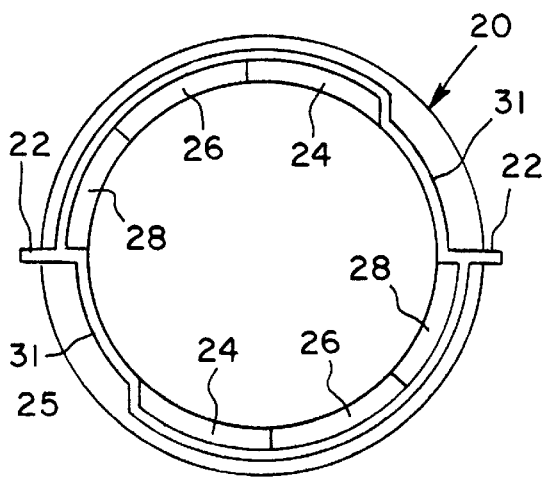
FIG. 6 is a horizontal cross-sectional view of the piston 20 corresponding to FIG. 5 taken along lines 6—6.
Figure 8:
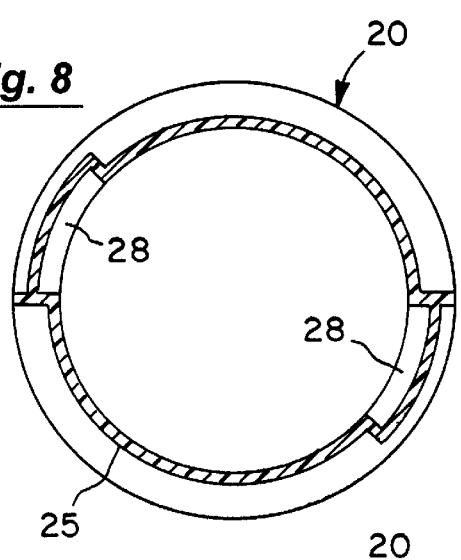
FIG. 8 is a horizontal cross-sectional view of the piston corresponding to FIG. 5 taken along lines 8—8.
Figure 10:
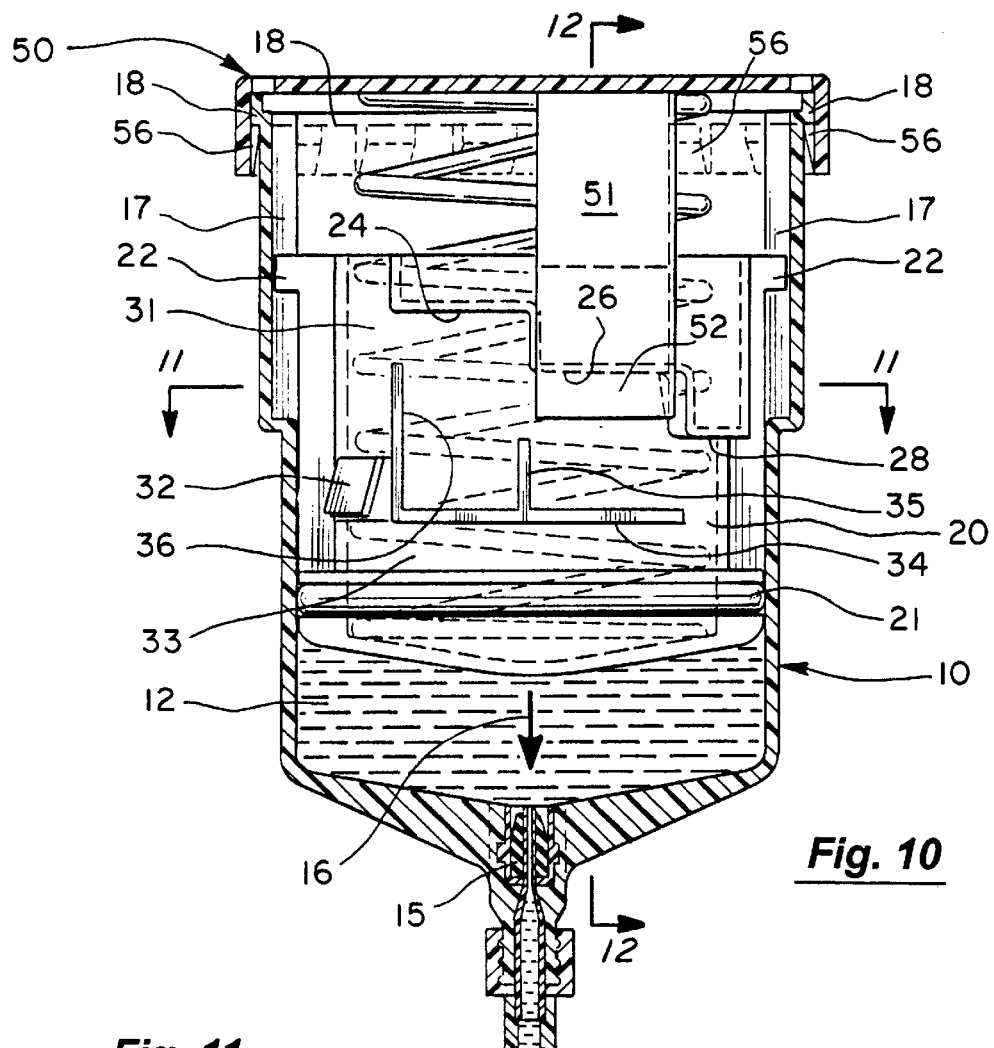
FIG. 10 is a vertical cross-sectional view of a second embodiment of the infusion pump employing a piston with a series of guides on the peripheral surface of the piston guiding the stop extending from the cap along the steps on the piston in a predetermined order.
Figure 11:
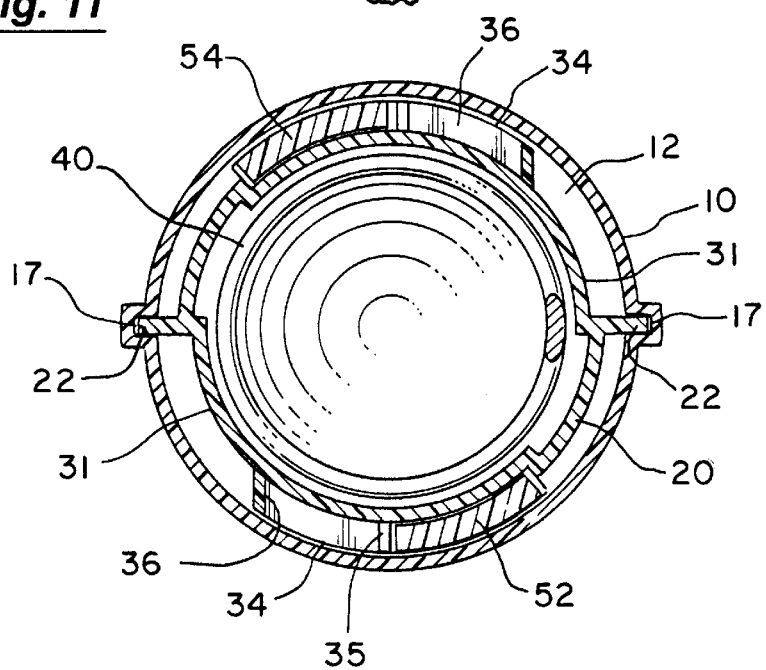
FIG. 11 is a horizontal cross-sectional view of the infusion pump corresponding to FIG. 10 taken along lines 11—11.
Figure 15:
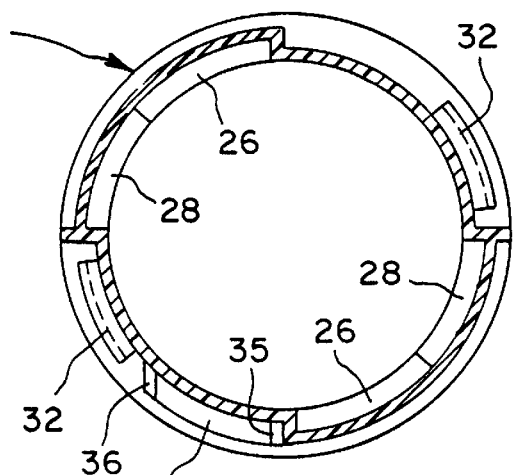
FIG. 15 is a horizontal cross-sectional view of the second embodiment of the piston 20 corresponding to FIG. 13 taken along lines 15—15.
Figure 14:
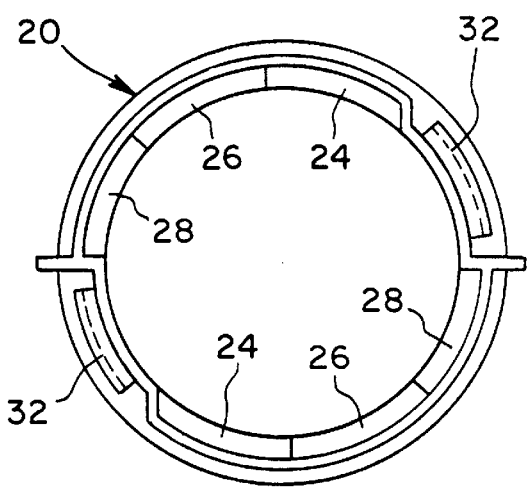
FIG. 14 is a horizontal cross-sectional view of the second embodiment of the piston 20 corresponding to FIG. 13 taken along lines 14—14.
Figure 16:
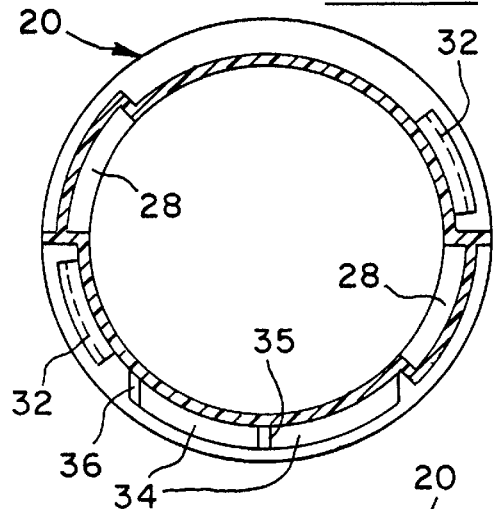
FIG. 16 is a horizontal cross-sectional view of the second embodiment of the piston 20 corresponding to FIG. 13 taken along lines 16—16.
Figure 13:
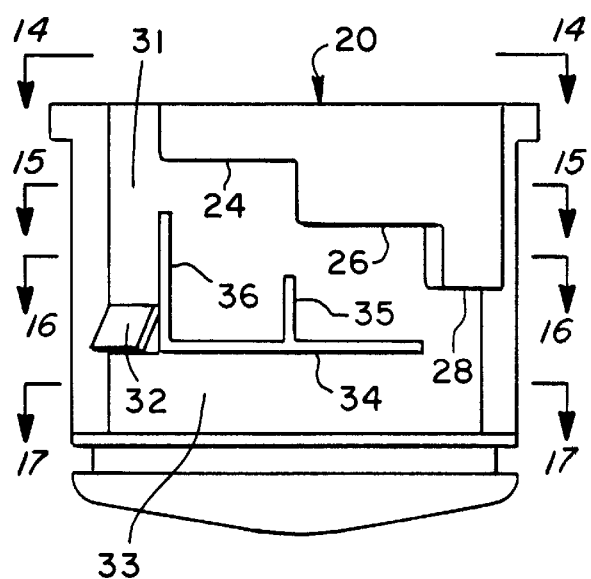
FIG. 13 is a side elevational view of the second embodiment of the piston 20.
Figure 17:
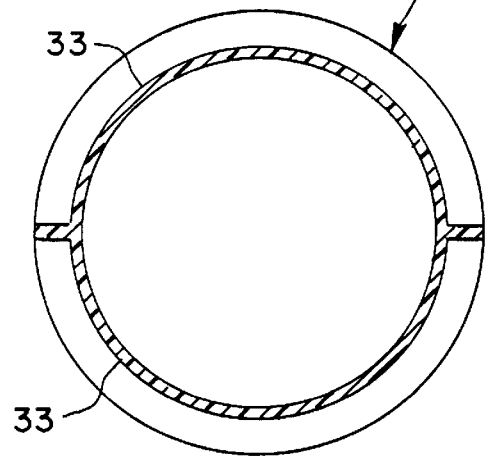
FIG. 17 is a horizontal cross-sectional view of the second embodiment of the piston 20 corresponding to FIG. 13 taken along lines 17—17.

A second embodiment of the infusion pump is shown in FIGS. 10–17 having a series of guides 34, 35, and 36 on the peripheral surface 25 of the piston 20 forward of the raised steps 24–28. In the first embodiment, there is nothing to prevent the entire dose of medication from being accidentally administered at once by rotating the cap 50 directly to the fourth rotational position. The guides 34–36 are intended to prevent this by guiding and limiting the path of the cap stops 52, 54 through each of the rotational positions in proper sequence. FIG. 10 is a vertical cross-sectional view of a second embodiment of the piston. FIGS. 11 and 12 are corresponding horizontal and vertical cross-sectional views. FIG. 13 is a side elevational view of the second embodiment of the piston 20. FIGS. 14–17 are corresponding horizontal cross-sectional views at various elevations.

In this second embodiment, each cap stop 52, 54 is initially aligned with a longitudinal guide slot 31 (see FIGS. 13 and 10) that allows the piston 20 to be fully retracted within the piston housing 10 as liquid is loaded under pressure into the chamber 12. As this occurs, each cap stop 52, 54 passes over an angled tab 32 in the longitudinal guide slot 31. The angled tab 32 allows the piston 20 to be freely retracted, but prevents the cap stop 52, 54 from being withdrawn via the longitudinal guide slot 31. This prevents the entire contents of the pump chamber 12 from accidentally being dispensed at one time. Instead, the healthcare provider must rotate the cap 50 so that the cap stop 52, 54 slides along a circumferential guide slot 33 (defined by a circumferential guide 34) until the stop 52, 54 is aligned with the first step 28. At this point, the piston 20 can move forward under pressure from the spring 40 until the stop 52, 54 comes into contact with the first step 28. The dosage of medication dispensed is proportional to the axial distance between the distal edge of the circumferential guide 34 and the first step 28.

After the first dose has been dispensed, the healthcare provider can dispense a second dose by rotating the cap 50 until the edge of the cap stop 52, 54 contacts the shorter longitudinal guide segment 35. This ensures that the stop 52, 54 is in axial alignment with the second step 26. At his point, the piston 20 moves forward once more until the stop 52, 54 comes into contact with the second step 26.

After the second dose has been dispensed, the healthcare provider can dispense a third dose by the rotating the cap 50 until the edge of the cap stop 52, 54 contacts the longer longitudinal guide segment 36. This moves the stop 52, 54 into axial alignment with the third step 24. The spring 40 can then move the piston 20 forward until the stop 52, 54 contacts the third step 24.

Finally, the healthcare provider can dispense the remaining liquid in the chamber 12 by rotating the cap until the cap stop 52, 54 slides past the proximal end of the longer longitudinal guide segment 36 and returns to the longitudinal guide slot 31 above the angled tab 32. This allows the piston to move forward until the pump chamber 12 is completely emptied.

It should be expressly understood that there are a wide range of possible variations based on the basic concept described above. For example, other drive means could be substituted for the coil spring shown in the drawings. Other types of springs or elastomeric materials could be used. Alternatively, the infusion pump could be manually actuated, or vacuum powered as disclosed by U.S. Pat. No. 5,135,500 (Zdeb).

As mentioned previously, the number of piston steps 24–28 and their spacing along the longitudinal axis of the piston can be designed to provide a variety of dose configurations. The number of steps 24–28 determine the maximum number of doses that can be dispensed without reloading the infusion pump. For example, a piston with one step can be used to dispense up to two doses. A piston with two steps can be used to dispense up to three doses. In general, a piston with N steps can be used to dispense up to N+1 doses.

In another embodiment, the raised steps 24–28 and guides 34–36 could protrude radially inward from the inside peripheral surface of the piston 20. The diameter between the arms 51, 53 extending forward from the cap 50 would be slightly smaller. The stops 52, 54 at the ends of the cap arms 51, 53 would point radially outward, rather than inward as shown in the figures. This embodiment would have the advantage of reducing any risk that the medication might leak and come into contact with the steps 24–28, guides 34–36, or the components of the cap 50 that could result in contamination.

In another embodiment, the placement of the piston steps 24–28 and cap stops 52, 54 could be reversed. The cap 50 can be equipped with a progression of inwardly-protruding steps that engage one or more stops extending outward from the peripheral surface 25 of the piston 20.

In yet another embodiment, the raised steps 24–28 could be replaced with grooves and/or steps that are recessed to varying degrees into the peripheral surface 25 of the piston 20. The cap arms 51, 53 would slide over the peripheral surface 25 of the piston, while the stops 52, 54 at the ends of the cap arms 51, 53 track the recessed grooves or steps.

The above disclosure sets forth a number of embodiments of the present invention. Other arrangements or embodiments, not precisely set forth, could be practiced under the teachings of the present invention and as set forth in the following claims.

I claim:

1. A multi-dose infusion pump comprising:
    a pump housing having an internal chamber extending along a longitudinal axis and a port for dispensing liquid from said chamber;
    a piston slidably engaging said chamber of said pump housing and having a peripheral surface;
    drive means urging said piston along said axis toward said port;
    a cap rotatably mounted to said pump housing;
    a plurality of steps spaced at intervals along said axis on one of said piston and said cap; and
    at least one stop on the other one of said piston and said cap, said stop engaging a selected one of said steps at each of a plurality of rotational positions for said cap, thereby selectively limiting axial movement of said piston toward said port to dispense a predetermined quantity of said liquid, and permitting a series of predetermined quantities of liquid to be dispensed by rotating said cap to align said stop with a sequence of said steps.

2. The infusion pump of claim 1 wherein said drive means comprises a spring between said piston and said cap.

3. The infusion pump of claim 1 wherein said steps are on said peripheral surface of said piston and said stop is on said cap.

4. The infusion pump of claim 3 wherein said cap further comprises an arm having a distal end extending toward said port, and wherein said stop is on said distal end of said arm.

5. The infusion pump of claim 3 wherein said steps comprise a sequence of steps extending in a radial pattern about at least a portion of said peripheral surface of said piston.

6. The infusion pump of claim 5 wherein said cap further comprises visual indicia showing proper rotational alignment between said stop and said steps.

7. The infusion pump of claim 5 wherein said piston further comprises a guide on said peripheral surface of said piston guiding said stop along said sequence of steps in a predetermined order.

8. The infusion pump of claim 7 wherein said guide further comprises an initial guide portion allowing said piston to be fully retracted toward said cap without engaging said stops while said cap is in a predetermined rotational position.

9. A multi-dose infusion pump comprising:

a pump housing having an internal chamber extending along a longitudinal axis and a port for dispensing liquid from said chamber;

a piston slidably engaging said chamber of said pump housing and having a peripheral surface with a sequence of steps spaced at intervals along said axis;

drive means urging said piston along said axis toward said port; and a cap rotatably mounted to said pump housing having at least one stop rotatably engaging a selected one of said steps at each of a plurality of rotational positions of said cap, thereby selectively limiting axial movement of said piston toward said port to dispense a predetermined quantity of said liquid, and permitting a series of predetermined quantities of liquid to be dispensed by rotating said cap to align said stop with a sequence of said steps.

10. The infusion pump of claim 9 wherein said drive means comprises a spring between said piston and said cap.

11. The infusion pump of claim 9 wherein said cap further comprises visual indicia showing proper rotational alignment between said stop and said steps.

12. The infusion pump of claim 9 wherein said cap further comprises an arm having a distal end extending toward said port, and wherein said stop extends from a distal portion of said arm.

13. The infusion pump of claim 9 wherein said sequence of steps extends in a radial pattern about at least a portion of said peripheral surface of said piston.

14. The infusion pump of claim 9 wherein said piston further comprises a guide on said peripheral surface of said piston guiding said stop along said sequence of steps in a predetermined order.

15. The infusion pump of claim 14 wherein said guide further comprises an initial guide portion allowing said piston to be fully retracted toward said cap without engaging said steps while said cap is in a predetermined rotational position.

16. A multi-dose infusion pump comprising:

a pump housing having an internal chamber extending along a longitudinal axis from a proximal opening to a distal port for dispensing liquid from said chamber;

a piston slidably engaging said chamber of said pump housing and having a peripheral surface with a sequence of raised steps in a radial pattern spaced at intervals along said axis;

a cap rotatably mounted over said proximal opening of said pump housing, said cap having:
 (a) an arm extending axially forward between said pump housing and said peripheral surface of said piston; and
 (b) a stop extending radially inward from said arm for engaging a selected one of said raised steps at each of a plurality of rotational positions of said cap, thereby selectively limiting axial movement of said piston within said chamber toward said distal port to dispense a predetermined quantity of said liquid; and a spring between said cap and said piston urging said piston along said axis toward said distal port.

17. The infusion pump of claim 16 wherein said cap further comprises visual indicia showing proper rotational alignment between said stop and said steps.

18. The infusion pump of claim 16 wherein said piston further comprises a guide on said peripheral surface of said piston guiding said stop along said sequence of steps in a predetermined order.

19. The infusion pump of claim 18 wherein said guide further comprises an initial guide portion allowing said piston to be fully retracted toward said cap without engaging said steps while said cap is in a predetermined rotational position.

20. A multi-dose infusion pump comprising:

a pump housing having an internal chamber extending along a longitudinal axis and a port for dispensing liquid from said chamber;

a cap rotatably mounted to said pump housing having at least one stop;

a piston slidably engaging said chamber of said pump housing and having a peripheral surface with:
 (a) a sequence of steps in a radial pattern on said peripheral surface and spaced at intervals along said axis, with said stop of said cap rotatably engaging a selected one of said steps at each of a plurality of rotational positions of said cap, thereby selectively limiting axial movement of said piston toward said port to dispense a predetermined quantity of said liquid, and permitting a series of predetermined quantities of liquid to be dispensed by rotating said cap to align said stop with a sequence of said steps; and
 (b) a guide extending on said peripheral surface of said piston, said guide allowing said piston to be fully retracted toward said cap without engaging said steps while said cap is in an initial rotational position and then guiding said stop along said sequence of steps in a predetermined order as said cap is rotated through a progression of subsequent rotational positions; and drive means urging said piston along said axis toward said port.

* * * * *